(12) United States Patent
Maschke et al.

(10) Patent No.: US 7,822,464 B2
(45) Date of Patent: Oct. 26, 2010

(54) GUIDEWIRE FOR VASCULAR CATHETERS

(75) Inventors: Michael Maschke, Lonnerstadt (DE); Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1126 days.

(21) Appl. No.: 11/291,593

(22) Filed: Nov. 30, 2005

(65) Prior Publication Data
US 2006/0116571 A1 Jun. 1, 2006

(30) Foreign Application Priority Data
Dec. 1, 2004 (DE) ........................ 10 2004 058 008

(51) Int. Cl.
*A61B 5/05* (2006.01)
(52) U.S. Cl. .................. 600/424; 128/899; 600/459; 600/462; 600/466; 600/585
(58) Field of Classification Search ............... 600/424, 600/459, 462, 466, 585
See application file for complete search history.

(56) References Cited

U.S. PATENT DOCUMENTS

| | | | |
|---|---|---|---|
| 4,770,185 A * | 9/1988 | Silverstein et al. .......... 600/454 |
| 5,365,943 A | 11/1994 | Jansen | |
| 5,549,109 A * | 8/1996 | Samson et al. ............. 600/381 |
| 5,596,996 A | 1/1997 | Johanson et al. | |
| 5,908,387 A * | 6/1999 | LeFree et al. ............... 600/425 |
| 6,233,476 B1 | 5/2001 | Strommer et al. | |
| 6,605,084 B2 * | 8/2003 | Acker et al. ................. 606/28 |
| 6,788,967 B2 | 9/2004 | Ben-Haim et al. | |
| 2001/0031919 A1 | 10/2001 | Strommer et al. | |
| 2001/0039418 A1 * | 11/2001 | Schaer ........................ 606/41 |
| 2002/0049375 A1 | 4/2002 | Strommer et al. | |
| 2003/0153827 A1 * | 8/2003 | Ritter et al. ................. 600/424 |
| 2004/0133225 A1 * | 7/2004 | Makower .................... 606/167 |
| 2004/0158142 A1 * | 8/2004 | Hall et al. ................... 600/374 |
| 2004/0210282 A1 * | 10/2004 | Flock et al. ................. 607/96 |
| 2004/0225213 A1 * | 11/2004 | Wang et al. ................. 600/421 |
| 2005/0119556 A1 * | 6/2005 | Gillies et al. ................ 600/410 |
| 2005/0245811 A1 * | 11/2005 | Scheffler ..................... 600/410 |
| 2005/0273020 A1 * | 12/2005 | Whittaker et al. ........... 600/585 |
| 2006/0229594 A1 * | 10/2006 | Francischelli et al. ........ 606/27 |
| 2006/0241572 A1 * | 10/2006 | Zhou ............................ 606/7 |

FOREIGN PATENT DOCUMENTS

| | | |
|---|---|---|
| DE | 42 15 901 A1 | 8/1993 |
| DE | 695 14 238 T2 | 2/1996 |
| DE | 102 24 011 A1 | 12/2003 |

OTHER PUBLICATIONS

US 5,924,990, 07/1999, Nachtomy et al. (withdrawn)

* cited by examiner

*Primary Examiner*—Long V Le
*Assistant Examiner*—Ellsworth Weatherby

(57) ABSTRACT

Guidewire for catheters which can be inserted into cavities, preferably coronary vessels of humans or animals, said guidewire being provided with electromagnetic receive or transmit locate to position its position in conjunction with corresponding external electromagnetic transmit or receive antennas, as well as with signal lines guiding the processing unit controlling the transmit antennas or transmit coils.

21 Claims, 2 Drawing Sheets

GUIDEWIRE FOR VASCULAR CATHETERS

CROSS REFERENCE TO RELATED APPLICATIONS

This application claims priority to the German application No. 10 2004 058 008.1, filed Dec. 1, 2004 which is incorporated by reference herein in its entirety.

FIELD OF INVENTION

The invention relates to a guidewire for catheters which can be inserted into cavities, preferably coronary vessels, of humans or animals.

BACKGROUND OF INVENTION

One of the most common fatal diseases is vascular disease, in particular cardiac infarction. This is caused by diseases of the coronary arteries (arteriosclerosis). With such diseases, deposits (atherosclerotic plaque) cause a 'blockage' in the coronary vessels.

A PTCA (Percutaneous transluminal coronary angioplasty) is used nowadays in the majority of cases if the coronary angiography shows severe narrowing (stenoses) of the coronary arteries, which cause angina pectoris, restrict a persons capability and/or endanger his/her life. For this purpose, the narrowings of the coronary vessels are dilated with the so-called "balloon catheter".

In this case, a maneuverable guidewire is typically guided through the vascular system starting from the femoral artery to the coronary narrowings to be treated. A guide catheter can then be pushed over the guidewire to the ostium of the coronary arteries. Within the guide catheter, a balloon catheter is fed over the guidewire ("Over-the-wire"). The balloon present at the distal end of the catheter is inflated until the stenosis is expanded.

This treatment of the coronary vessels has essentially been carried out previously by means of a coronary angiography using contrast means subject to x-ray control. The disadvantage of this method is that only the vessel diameter and/or the narrowing which can be used by the blood flow is displayed here as a two-dimensional silhouette. The guidewire and the catheter are similarly displayed as a two-dimensional overlay image within the angiographic x-ray image. The disadvantage with this method is that the guidewire, catheter and organic tissue are displayed with different qualities in the x-ray image. As a rule, the x-ray system can only be optimized to one object type, typically the organic tissue. An effective display of all objects is desirable both for patients and medical staff, in particular with a spatial assignment in patients and a reduction of x-ray radiation.

U.S. Pat. No. 5,596,996 describes a heavy loadable guidewire made of a tubular nitinol having transition elements made of plastic with a diameter of 0.25 mm to 0.35 mm, this being provided with a marker band to improve visibility. This also only achieves a slight improvement in the two-dimensional overlay image. U.S. Pat. No. 5,365,943 describes an anatomically adjusted maneuverable PTKA guidewire which can be inserted easily but does not achieve an improvement in the visibility.

A new imaging method is already used in several clinics. In this case, an IVUS catheter is inserted into the coronary vessel and is subsequently pulled back out of the vessel ("pullback"). The method is described for example in U.S. Pat. No. 5,924,990. The disadvantage of this method lies in the additional catheter which has to be pushed into the vessel in order to obtain these photos. As above, these are again only two-dimensional images. This catheter has to be removed again before the guidewire for the balloon catheter can be inserted.

A device displaying the guidewire in spatial association to the human body using a low radiation dose is desirable. A guidewire which is inserted in the human vascular system is used with the majority of medical aids. Furthermore, the guidewire is advantageous in that, in contrast with other medical aids, it remains in the patient throughout the medical procedure until the procedure has ended. Other medical instruments, such as guide catheters, balloon catheters, catheters for positioning stents, are only inserted for the specific part of the application. Furthermore, a guidewire is relatively cost-effective to manufacture in comparison with other medical devices.

DE 42 15 901 A1 discloses a catheter with a locatable end region. As mentioned above however, this solution involves a catheter rather than a guidewire. Furthermore, this solution is disadvantageous in that the human body is assumed as the model of an endless, homogenous, conductible half-space and that additionally the measuring device has to be positioned in a shielding chamber.

A system is known from a further patent application which provides 3D images from IVUS and OCT. Nevertheless this system is also a catheter which is moreover equipped with relatively expensive sensors.

U.S. Pat. No. 6,233,476 (Medical Positioning System, Strommer et al.), US 2001/0031919 (Medical Imaging Navigation System, Strommer et al.), US 2002/0049375 (Method and Apparatus for Real Time Quantitative Three-Dimensional Image Reconstruction of a Moving Organ and Intra-Body Navigation, Strommer et al.) describes a spatial positioning of a medical catheter partially in combination with an IVUS sensor. The main disadvantage of this device is that in this case it is not a guidewire which can be used for a multiplicity of medical aids, but is instead a special catheter which is inserted into the body and only allows special medical applications and must be withdrawn from the body when the medical aid is changed.

SUMMARY OF INVENTION

An object underlying the invention is thus to design a guidewire such that it can be positioned in a simple and precise manner, so that with the aid of a guide wire remaining in the body throughout a long examination period, the actual working catheter, which in its turn can be embodied without the need for any complicated navigation devices, can be very easily positioned.

To achieve this object provision is made in accordance with the invention for the guidewire to be provided with electromagnetic receive and transmit coils in order to locate its position in conjunction with corresponding external electromagnetic transmit and/or receive antennas and also with signal lines guiding the processing unit controlling the transmit antennas or coils.

The inventive equipping of the guidewire, preferably with receive coils which record signals from external antennas, allows a very precise positioning which not only facilitates the advance of the guidewire, but above all allows the position to be displayed in medical images acquired in other ways, for instance 3D images, as can be generated with the aid of a mobile C-arm device.

To achieve an even better miniaturization, provision can be made according to a further feature of the invention to arrange the coils not exclusively orthogonally, but at any other angle, for instance 60°, thereby allowing the position sensors to be inserted far more effectively into the guidewire. The deviation from the orthogonal arrangement is corrected by the corresponding computing algorithms in the image processing device.

In order to improve the miniaturization, only one electrical conductor per sensor coil is fed back to the signal interface links in each instance. The conductive guidewire and the human body with its blood vessels are used as "neutral electrodes". In addition, a signal multiplexer can be integrated into the tip of the guidewire, said signal multiplexer cyclically interrogating the receive antenna which results in a further reduction in the signaling lines.

Moreover, nanotechnology can be used to further increase the miniaturization.

For calibration purposes, the tip of the guidewire is recorded at least once by means of at least two x-ray projections in the chamber (x, y, z) and the position in the chamber is determined at least once by the magnetic positioning system (x', y', z'). The transformation allows the two positions to be calibrated together one after the other. It is advantageous for the calibration to be carried out only following installation in the clinic. The use of the body phantom and a calibration with several points can increase the accuracy of the calibration.

The image information of the guidewire acquired using the position sensors is added and/or superimposed using 3D-images (registration, fusion). These 3D x-ray images are generated using methods of the discrete tomography from minimal projections. A method for discrete tomography is described for instance in DE 102 24 011 ("Computerized reconstruction method for a three-dimensional object", Hornegger, Schnörr et al). This is advantageous in that the patient and the clinical personnel are only exposed to a minimal exposure dose.

The spatial coordinates of both objects need to be transferred into a common coordinate system in order to register (superimpose) the image data of the patient with the position data. Movements of the patient on the examination table are determined in U.S. Pat. No. 6,233,476 using a magnetic auxiliary sensor. Alternatively it is proposed to detect the position of the patient by means of an optical camera and to determine the patients' movements/displacements using computerized methods of pattern recognition and to correct these in the image processing unit. Additionally the patient can be scanned using a laser beam thereby determining and correcting the position displacement.

Provision is made in one embodiment of the invention such that the guidewire is woven together from individual strands, of which at least one is provided with an insulation and serves as a signal line for the receive or transmit coils. With regard to the preferred use of receive coils in the guidewire, the following only refers simplistically to these receive coils and reference is not made each time such that an exchange would be possible in which transmit coils are accommodated in the guidewire to which external receive antennas are assigned.

This integration of signal lines into the guidewire is thus completely uncomplicated, since the structure is made of individual strands woven together and in any event is the preferred structure of a guidewire of this type in respect of a desired flexibility on the one hand and of a displacement rigidity on the other hand.

In the field of the invention, provision is thus further made for the guidewire to be provided with a slide coating which serves to ease the movement of the catheters, for example a silicon coating or a coating in the form of a hydrophilic coating.

In order to prevent magnetic fields from influencing the signals, in particular the magnetic fields of the transmit antennas, the signal lines are to be provided with shields against magnetic fields, for example by embodying the signal lines as grounded coaxial cables.

To enable the guidewire to be magnetically navigated, provision can be made for electromagnets or permanent magnets for strong external magnetic fields, which can be realized in a particularly favorable manner, such that the magnetic receive coils optionally provided with iron cores for position determination purposes can be optionally operated for the magnetic navigation as receive antennas or as electromagnets.

In order to prevent the magnetic fields induced by the navigation magnets from falsifying the measurement results of the magnetic positioning system (transmitter and receiver), provision can be made in accordance with a further feature of the present invention for the processing device to comprise a storage device for recording the field line curves of the navigation magnet system following the system installation, so as to enable said storage device to be used during the reconstruction of the magnetic position vectors for correction purposes.

To increase the accuracy of the positioning, it is possible to operate and evaluate the transmit coils cyclically at specific time segments with different frequencies. Furthermore, it would also be possible to install additional ultrasonic sensors in the tip. In addition to an arrangement, in which an ultrasonic sensor is supported so that it can rotate, a number of annular US sensors can be arranged in a distributed fashion and scanned cyclically by means of a multiplexer.

Finally, provision is made within the field of the invention to install an OCT and/or IVUS image sensor in the tip of the guidewire such that at least individual signal links are configured wirelessly, in particular with a Bluetooth transmit unit, so that fewer cable links to the patient are needed.

In addition to the possibility of providing the guidewire with markings which are easily visible in the x-ray image, a further favorable representation of the progress of the guidewire also exists in the embodiment of the invention, in that an envelope curve and from this the vessel centerline are able to be calculated from the boundary points when its tip comes into contact with the vessel wall, in other words from the specific boundary positions of the tip of the guidewire in each instance.

BRIEF DESCRIPTION OF THE DRAWINGS

Further advantages, features and details of the invention are set down in the description below of an exemplary embodiment with reference to the drawings, in which.

DETAILED DESCRIPTION OF INVENTION

Figure 1:
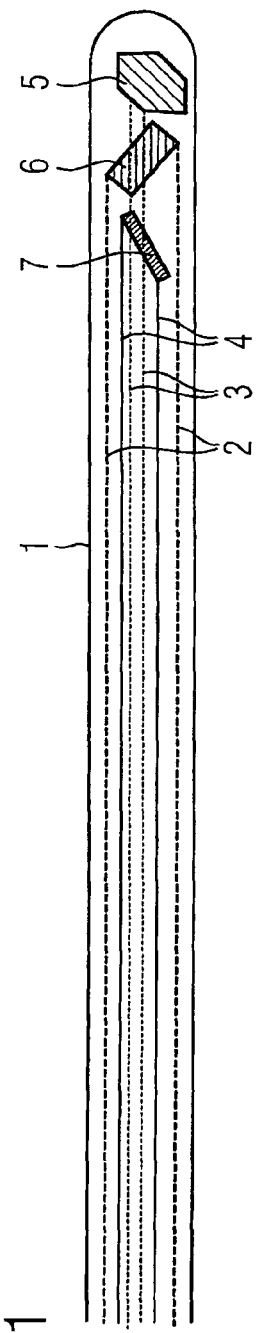
FIGS. 1 and 2 show schematic representations of a guidewire with differently embodied signal lines for the receive coils.

The guidewire with an external guidewire housing 1 illustrated schematically in FIG. 1 contains paired signal lines 2, 3, and 4 at receive coils 5, 6 and 7 aligned to the x-, y- and z-direction. Contrastingly, with the exemplary embodiment according to FIG. 2, the receive coils 5, 6, and 7 are linked on the one side to the external guidewire housing 1, so that only one signal line is to be recirculated to each receive coil which is preferably embodied as an insulated individual strand which is woven together to the guidewire using further individual strands.

Figure 2:
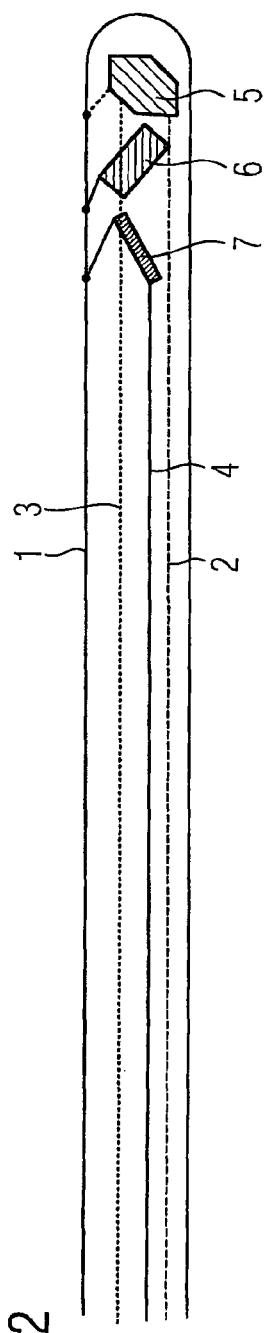
Figure 3:
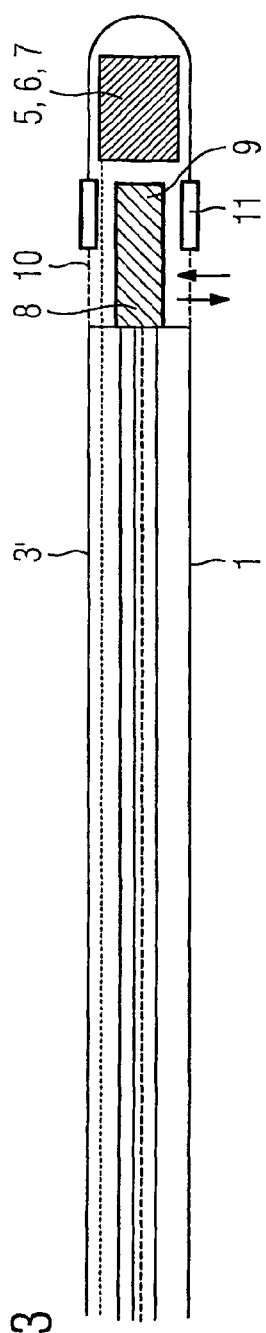
FIG. 3 shows a schematic representation of a guidewire containing an additional OCT-IVUS combination

In addition to the receive coils 5 to 7 illustrated in FIGS. 1 and 2, which are only shown as small boxes in FIG. 3 with the signal lines deriving therefrom not being shown in any more detail, but instead only with reference to a schematically indicated signal line 3, the guidewire according to FIG. 3 additionally features an OCT sensor 8 and an IVUS sensor 9 which are arranged respectively within an OCT viewing window 10 and/or a transparent window 11 for ultrasound in the external guidewire housing 1 of the guidewires.

Figure 4:
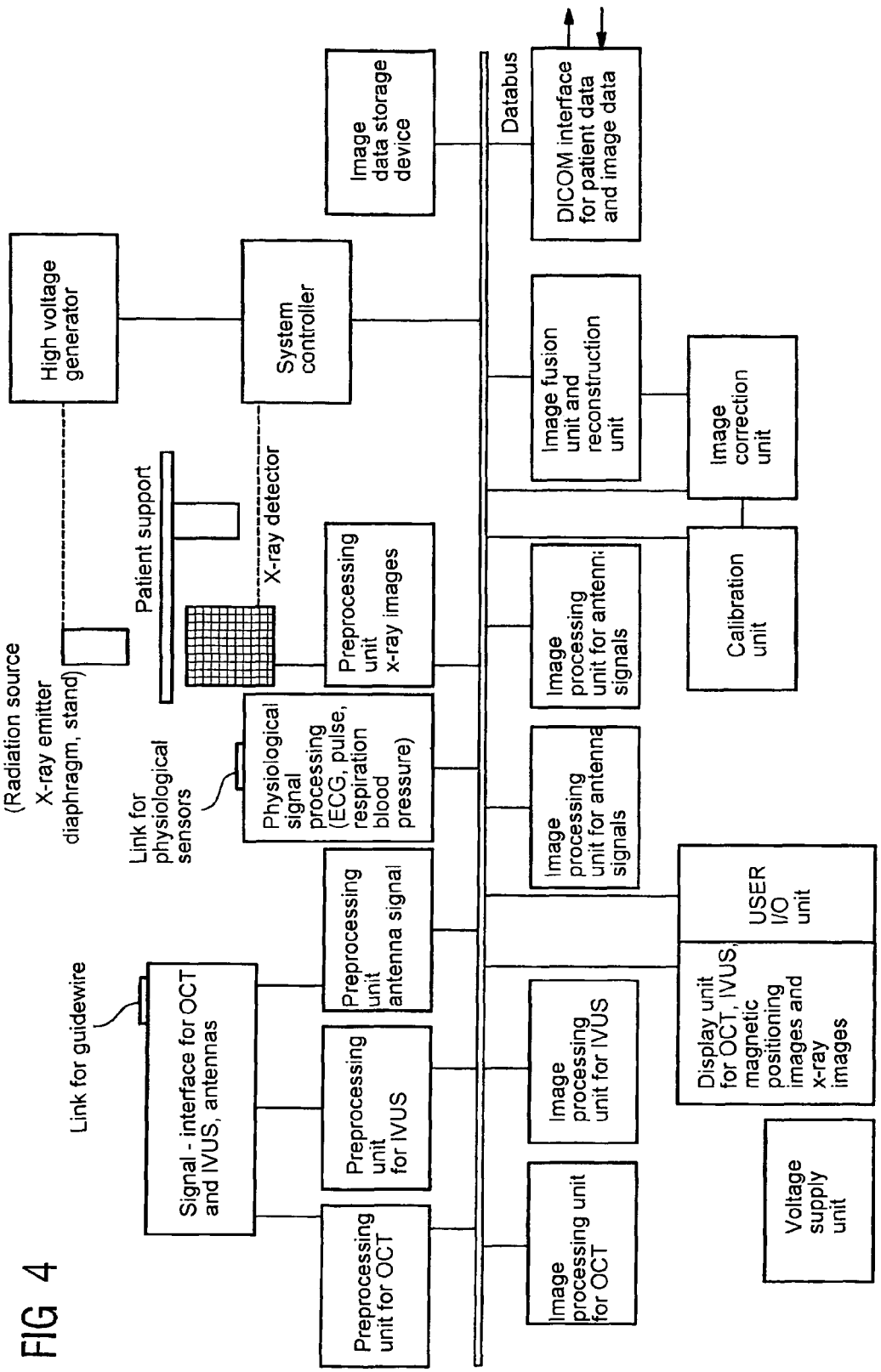
FIG. 4 shows a schematic system diagram of an examination device using a guidewire according to the invention.

The use of a guidewire of this type in an examination device having an x-ray device results from the system diagram in FIG. 4, in which only the transmit coils surrounding the patient support for determining the position of the guidewire are not shown.

The invention claimed is:

1. A guidewire system, comprising:
    a catheter; and
    a guidewire, wherein said guidewire comprises:
        an external guidewire housing configured to guide the catheter within a vascular cavity;
        a plurality of electromagnetic receiver or transmitter coils arranged within the external guidewire housing wherein the receiver or transmitter coils are configured to locate a position of the guidewire within the vascular cavity via cooperation with corresponding external electromagnetic transmitter or receiver antennas;
        signal lines arranged within the external guidewire housing connecting the plurality of electromagnetic receiver or transmitter coils to a processing unit that controls the transmitter coils or the transmitter antennas;
        a plurality of ultrasonic sensors distributed across and arranged annularly around and within the external guidewire housing; and
        a multiplexer configured to cyclically scan the plurality of ultrasonic sensors;
        wherein one side of each of the plurality of electromagnetic receiver or transmitter coils are linked to the external guidewire housing so that only one signal line is used for each of the plurality of electromagnetic receiver or transmitter coils, and
        wherein the guidewire is provided with a slide coating for easing the movement of the catheter over the guidewire.

2. The guidewire system according to claim 1, wherein the vascular cavity is within a coronary vessel of a human.

3. The guidewire system according to claim 1, wherein the guidewire includes woven individual strands, at least one individual strand having an insulation and operating as a signal line for the receiver coils.

4. The guidewire system according to claim 1, wherein the slide coating is a silicon coating.

5. The guidewire system according to claim 1, wherein the slide coating is a hydrophilic coating.

6. The guidewire system according to claim 1, wherein the signal lines include shields against magnetic fields.

7. The guidewire system according to claim 6, wherein the shields are configured to shield magnetic fields generated by the transmitter antennas.

8. The guidewire system according to claim 7, wherein the signal lines are grounded coaxial cables.

9. The guidewire system according to claim 1, further comprising a navigation system having electromagnets or permanent magnets for navigating the guidewire using external magnetic fields.

10. The guidewire system according to claim 9, wherein the receiver coils are both a receiving device and the electromagnets.

11. The guidewire system according to claim 9, wherein the signal lines are configured to connect to the processing unit where the processing unit comprises a storage device for recording field line curves of the navigation system upon commissioning of the navigation system.

12. The guidewire system according to claim 11, wherein the processing unit reconstructs magnetic position vectors from the recorded field line curves.

13. The guidewire system according to claim 1, wherein the electromagnetic receiver or transmitter coils operate cyclically using different frequencies.

14. The guidewire system according to claim 1, wherein the ultrasonic sensors are rotatably supported.

15. The guidewire system according to claim 1, further comprising an OCT or an IVUS image sensor arranged at a tip of the guidewire.

16. The guidewire system according to claim 1, wherein the guidewire further comprises a wireless link device wherein at least some individual signal links are established wirelessly.

17. The guidewire system according to claim 16, wherein the wireless signal links are established using a Bluetooth transmitter unit.

18. The guidewire system according to claim 1, wherein an acquired position of the guidewire and image information is added or superimposed with other medical images using the processing unit.

19. The guidewire system according to claim 1, wherein the guidewire further comprises markings visible in an x-ray image.

20. The guidewire system according to claim 1, wherein the signal lines are configured to connect to the processing unit where the processing unit is configured to calculate an envelope curve and a vascular centerline based on the envelope curve using boundary points acquired when a tip of the guidewire comes into contact with a vessel wall.

21. The guidewire system according to claim 1, wherein the electromagnetic receiver or transmitter coils are angled about the guidewire to enable the electromagnetic receiver or transmitter coils to facilitate insertion into the guidewire.

* * * * *